US007943620B2

(12) United States Patent
Harbeson et al.

(10) Patent No.: US 7,943,620 B2
(45) Date of Patent: May 17, 2011

(54) ANTI-ANGINAL COMPOUNDS

(75) Inventors: Scott L. Harbeson, Cambridge, MA (US); Craig Masse, Cambridge, MA (US)

(73) Assignee: Concert Pharmaceuticals, Inc., Lexington, MA (US)

( * ) Notice: Subject to any disclaimer, the term of this patent is extended or adjusted under 35 U.S.C. 154(b) by 152 days.

(21) Appl. No.: 12/075,107

(22) Filed: Mar. 7, 2008

(65) Prior Publication Data

US 2008/0318969 A1 Dec. 25, 2008

Related U.S. Application Data

(60) Provisional application No. 60/893,494, filed on Mar. 7, 2007.

(51) Int. Cl.
A61K 31/497 (2006.01)
C07D 241/04 (2006.01)
C07D 295/00 (2006.01)

(52) U.S. Cl. .................................. 514/252.12; 544/400

(58) Field of Classification Search ............. 514/252.12; 544/400, 40
See application file for complete search history.

(56) References Cited

U.S. PATENT DOCUMENTS

| | | | |
|---|---|---|---|
| 4,567,264 A | 1/1986 | Kluge et al. | |
| 6,221,335 B1 * | 4/2001 | Foster | 424/1.81 |
| 6,303,607 B1 | 10/2001 | Wolff et al. | |
| 6,333,342 B1 | 12/2001 | Foster | |
| 6,369,062 B1 | 4/2002 | Wolff et al. | |
| 6,440,710 B1 * | 8/2002 | Keinan et al. | 435/148 |
| 6,479,496 B1 | 11/2002 | Wolff | |
| 6,503,911 B2 | 1/2003 | Wolff et al. | |
| 6,525,057 B2 | 2/2003 | Wolff et al. | |
| 6,562,826 B1 | 5/2003 | Wolff | |
| 6,603,008 B1 * | 8/2003 | Ando et al. | 546/269.7 |
| 6,617,328 B2 | 9/2003 | Wolff et al. | |
| 6,620,814 B2 | 9/2003 | Wolff et al. | |
| 6,852,724 B2 | 2/2005 | Wolff | |
| 6,864,258 B2 | 3/2005 | Wolff | |
| 7,517,990 B2 * | 4/2009 | Ito et al. | 546/184 |
| 2005/0069276 A1 | 3/2005 | Alken | |
| 2007/0082929 A1 * | 4/2007 | Gant et al. | 514/338 |
| 2007/0197695 A1 * | 8/2007 | Potyen et al. | 524/110 |
| 2008/0103122 A1 | 5/2008 | Veltri | |
| 2008/0312247 A1 | 12/2008 | Gant et al. | |
| 2009/0076018 A1 | 3/2009 | Czarnik | |

FOREIGN PATENT DOCUMENTS

| | | |
|---|---|---|
| EP | 0 126 449 A1 | 11/1984 |
| EP | 0126449 * | 11/1984 |
| WO | WO 95/26325 A2 | 10/1995 |
| WO | WO 2007/118651 A1 | 10/2007 |
| WO | WO 2008/109175 A1 | 9/2008 |

OTHER PUBLICATIONS

Tonn, Biological Mass Spectrometry vol. 22 Issue 11, pp. 633-642 (1993).*
Dyck, Journal of Neurochemistry vol. 46 Issue 2, pp. 399-404 (1986).*
Haskins, Biomedical Spectrometry vol. 9 Issue 7, pp. 269-277 (1982).*
Wolen, Journal of Clinical Pharmacology 1986; 26: 419-424.*
Browne, Journal of Clinical Pharmacology1998; 38: 213-220.*
Baillie, Pharmacology Rev.1981; 33: 81-132.*
Gouyette, Biomedical and Environmental Mass Spectrometry, vol. 15, 243-247 (1988).*
Cherrah, Biomedical and Environmental Mass Spectrometry vol. 14 Issue 11, pp. 653-657 (1987).*
Pieniaszek, J Clin Pharmacol.1999; 39: 817-825.*
Honma et al., Drug Metab Dispos 15 (4): 551 (1987).*
PCT International Search Report for International Application No. PCT/US2008/003183, Date of Mailing: Aug. 6, 2008.
PCT Written Opinion of the International Searching Authority for International Application No. PCT/US2008/003183, Date of Mailing: Aug. 6, 2008.
Fisher, M.B. et al., "The Complexities Inherent in Attempts to Decrease Drug Clearance by Blocking Sites of CYP-Mediated Metabolism," *Curr. Opin. Drug Discov.*, 9(1): 101-109 (Jan. 2006).
Foster, A.B., "Deuterium Isotope Effects in the Metabolism of Drugs and Xenobiotics: Implications for Drug Design," *Advances in Drug Research*, Academic Press, London, GB, vol. 14, Jan. 1, 1985, pp. 1-40, XP009086953.
Kushner, D.J. et al., "Pharmacological Uses and Perspectives of Heavy Water and Deuterated Compounds," *Can. J. Physiol. Pharmacol.*, 77(2): 79-88 (Feb. 1999).
U.S. Prescribing Information for Ranexa®, downloaded on Jan. 29, 2009 from http://www.cvt.com/a_products_ranexa.html, CV Therapeutics, Inc., Palo Alto, CA, pp. 1-13.
Notification Concerning Transmittal of International Preliminary Report on Patentability, International Application No. PCT/US2008/003183, Date of Mailing Sep. 17, 2009.
Foster, A. B., "Deuterium Isotope Effects in Studies of Drug Metabolism," *Trends in Pharmacological Sciences*, 5: 524-527 (1984).
Herron, W. J., et al., "Estimation of Ranolazine and Eleven Phase I Metabolites in Human Plasma by Liquid Chromatography-Atmospheric Pressure Chemical Ionisation Mass Spectrometry with Selected-Ion Monitoring," *Journal of Chromatography A*, 712: 55-60 (1995).
Penman, A. D., et al., "The Characterization of the Metabolites of Ranolazine in Man by Liquid Chromatography Mass Spectrometry," *Rapid Communications in Mass Spectrometry*, 9: 1418-1430 (1995).
Office Communication, European Patent Application No. 08726679.7, Date of Mailing Jan. 12, 2010.

* cited by examiner

*Primary Examiner* — James O Wilson
*Assistant Examiner* — Erich A Leeser
(74) *Attorney, Agent, or Firm* — Hamilton, Brook, Smith & Reynolds, P.C.

(57) ABSTRACT

This invention relates to novel compounds that partially inhibit fatty acid oxidation and pharmaceutically acceptable salts thereof. More specifically, this invention relates to novel compounds that are derivatives of ranolazine. This invention also provides compositions comprising one or more compound of this invention and a carrier and the use of the disclosed compounds and compositions in methods of treating diseases and conditions that are beneficially treated by partial fatty acid oxidation inhibitors, such as ranolazine.

31 Claims, No Drawings

ANTI-ANGINAL COMPOUNDS

RELATED APPLICATION

This application claims the benefit of U.S. Provisional Application No. 60/893,494, filed on Mar. 7, 2007. The entire teachings of the above application(s) are incorporated herein by reference.

BACKGROUND OF THE INVENTION

Ranolazine, also known as 1-[3-(2-Methoxyphenoxy)-2-hydroxypropyl]-4-[(2,6-dimethylphenyl)aminocarbonylmethyl]piperazine; and N-(2,6-Dimethylphenyl)-4-[2-hydroxy-3-(2-methoxyphenoxy)propyl]piperazine-1-acetamide is a partial fatty acid oxidation (PFOX) inhibitor. Its synthesis is described in U.S. Pat. No. 4,567,264.

Ranolazine is an orally dosed compound with anti-anginal and anti-ischemic effects without reductions in heart rate or blood pressure. Its mechanism of action is not known, but it is believed to be an ion channel inhibitor (see Pharmacology Review CDER Approval Package for Application Number NDA 21-526 and Antzelevitch, C et al., Circulation 2004, 110, p. 904-910), even though there is no clear understanding of the electrophysiology of the compound and its efficacy in stable angina. Recent publications have reported data supporting ranolazine as an inhibitor of late sodium current, which could explain its cardiovascular activity (see Undrovinas, A I et al, J Cardiovasc Electrophysiol 2006, 17:S169; Hale S L et al, J Pharmacol Exp Ther 2006, 31:418 and Fredj S et al, Br J Pharmacol 2006, 148:16).

Ranolazine has been evaluated in clinical trials for patients with chronic angina who remain symptomatic despite treatment with the maximum dose of another anti-angina agent. Statistically significant reductions in angina attack frequency and nitroglycerine use have been shown clinically. Clinical studies have also shown statistically significant increases in exercise duration and time to angina. See Stone P H et al., J Am Coll Cardiol 2006, 48, 566; Chaitman, B R et al., Circulation 2002, 106(19, Suppl. 2): Abst 1649; and the label approved for NDA no. 021526, Drugs@FDA.gov website.

Ranolazine has been approved for treatment of chronic angina in patients who have not achieved adequate response with other anti-anginal drugs. It is approved for use in combination with other anti-anginal drugs, including calcium channel blockers, beta-blockers, and nitrates. It is also currently in phase III trials in the US for treatment of unstable angina (acute coronary syndrome).

Despite the beneficial activities of ranolazine, there is a continuing need for new compounds to treat the aforementioned diseases and conditions.

SUMMARY OF THE INVENTION

This invention relates to novel compounds that partially inhibit fatty acid oxidation and pharmaceutically acceptable salts thereof. More specifically, this invention relates to novel compounds that are derivatives of ranolazine. This invention also provides compositions comprising one or more compound of this invention and a carrier and the use of the disclosed compounds and compositions in methods of treating diseases and conditions that are beneficially treated by partial fatty acid oxidation inhibitors, such as ranolazine.

DETAILED DESCRIPTION OF THE INVENTION

The terms "ameliorate" and "treat" are used interchangeably and include both therapeutic treatment and prophylactic treatment (reducing the likelihood of development). Both terms mean decrease, suppress, attenuate, diminish, arrest, or stabilize the development or progression of a disease (e.g., a disease or disorder delineated herein), lessen the severity of the disease or improve the symptoms associated with the disease.

The term "partial fatty acid oxidation inhibitor" refers to a compound that suppresses ATP production from the oxidation of fatty acids and consequently stimulates ATP production form the oxidation of glucose and lactate.

"Disease" means any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of ranolazine will inherently contain small amounts of deuterated and/or $^{13}$C-containing isotopologues. The concentration of naturally abundant stable hydrogen and carbon isotopes, notwithstanding this variation, is small and immaterial as compared to the degree of stable isotopic substitution of compounds of this invention. See, for instance, Wada E et al., Seikagaku 1994, 66:15; Ganes L Z et al., Comp Biochem Physiol Mol Integr Physiol 1998, 119: 725.

The compounds of the present invention are distinguished from such naturally occurring minor forms in that the term "compound" as used in this invention refers to a composition of matter that has a minimum isotopic enrichment factor of at least 500 (7.5% deuterium incorporation) for each deuterium atom that is present at a site designated as a site of deuteration in Formula (I) and Formula A.

In the compounds of the invention, any atom not specifically designated as a particular isotope is meant to represent any stable isotope of that atom unless otherwise stated. Unless otherwise stated, when a position is designated specifically as "H" or "hydrogen," the position is understood to have hydrogen at its natural abundance isotopic composition.

The term "isotopic enrichment factor" as used herein means the ratio between the isotopic abundance (e.g., D or $^{13}$C) at a specified position in a compound of this invention and the naturally occurring abundance of that isotope. The natural abundance of deuterium is 0.015%. The natural abundance of $^{13}$C is 1.11%.

In other embodiments, a compound of this invention has an isotopic enrichment factor for each deuterium present at a site designated as a potential site of deuteration on the compound of at least 1000 (15% deuterium incorporation), at least 1500 (22.5% deuterium incorporation), at least 2000 (30% deuterium incorporation), at least 2500 (37.5% deuterium incorporation), at least 3000 (45% deuterium incorporation), at least 3500 (52.5% deuterium incorporation), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). It is understood that the isotopic enrichment factor of each deuterium present at a site designated as a site of deuteration is independent of other deuterated sites. For example, if there are two sites of deuteration on a compound one site could be deuterated at 22.5% while the other could be deuterated at 37.5% and still be considered a compound wherein the isotopic enrichment factor is at least 1500 (22.5%).

The structural formula depicted herein may or may not indicate whether atoms at certain positions are isotopically enriched. In a most general embodiment, when a structural formula is silent with respect to whether a particular position is isotopically enriched, it is to be understood that the stable isotopes at the particular position are present at natural abundance, or, alternatively, that that particular position is isotopically enriched with one or more naturally occurring stable isotopes. In a more specific embodiment, the stable isotopes are present at natural abundance at all positions in a compound not specifically designated as being isotopically enriched.

The term "isotopologue" refers to a species that differs from a specific compound of this invention only in the isotopic composition thereof. Isotopologues can differ in the level of isotopic enrichment at one or more positions and/or in the positions(s) of isotopic enrichment.

The term "compound," as used herein, is also intended to include solvates or hydrates thereof.

A salt of a compound of this invention is formed between an acid and a basic group of the compound, such as an amino functional group, or a base and an acidic group of the compound, such as a carboxyl functional group. Accordingly, in one embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

As used herein, the term "hydrate" means a compound which further includes a stoichiometric or non-stoichiometric amount of water bound by non-covalent intermolecular forces.

As used herein, the term "solvate" means a compound which further includes a stoichiometric or non-stoichiometric amount of solvent such as water, acetone, ethanol, methanol, dichloromethane, 2-propanol, or the like, bound by non-covalent intermolecular forces.

The compounds of the present invention (e.g., compounds of Formula I) contain an asymmetric carbon. Accordingly, compounds of this invention can exist as either individual enantiomers (e.g., one of (S) or (R)), or mixtures of the two enantiomers. A compound of the present invention will include both racemic mixtures, and also individual respective stereoisomers that are substantially free from another possible stereoisomer. The term "substantially free of other stereoisomers" as used herein means less than 25% of other stereoisomers, less than 10% of other stereoisomers, less than 5% of other stereoisomers, less than 2% of other stereoisomers, or less than "X"% of other stereoisomers (wherein X is a number between 0 and 100, inclusive) are present. Methods of obtaining or synthesizing an individual enantiomer for a given compound are well known in the art and may be applied as practicable to final compounds or to starting material or intermediates.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" refers to deuterium.

"Stereoisomer" refers to both enantiomers and diastereomers.

Throughout this specification, reference to "each R" includes, independently, any "R" group (e.g., $R^1$, $R^2$, $R^3$, $R^4$, and $R^5$) where applicable.

Therapeutic Compounds

The present invention provides a compound of Formula A:

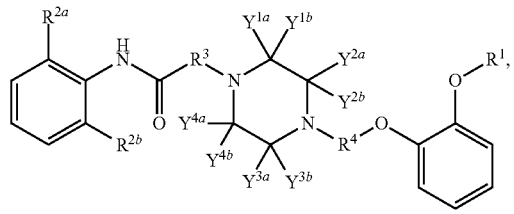

or a pharmaceutically acceptable salt thereof wherein:

each of $R^1$, $R^{2a}$, and $R^{2b}$ is independently selected from —$CH_3$, —$CDH_2$, —$CD_2H$, and —$CD_3$;

$R^3$ is selected from —$CH_2$—, —$CDH$—, and —$CD_2$-;

$R^4$ is —$C(R^5)_2$—$CR^5OH$—$C(R^5)_2$—, wherein each $R^5$ is independently selected from D and H;

each Y is independently selected from D and H; and when each Y is H, at least one R contains a deuterium atom.

In another embodiment, the invention provides a compound of Formula I:

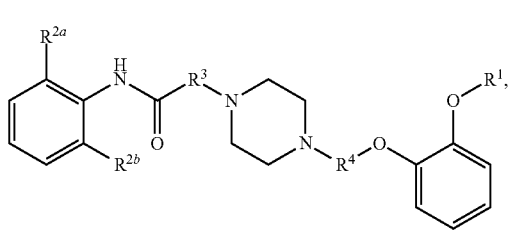

(I)

or a pharmaceutically acceptable salt thereof, wherein each R is defined as above for Formula A, and at least one R contains a deuterium atom.

In one embodiment of Formula A or Formula I, $R^1$ is —$CD_3$ or —$CH_3$.

In another embodiment of Formula A or Formula I, each of $R^{2a}$ and $R^{2b}$ is independently selected from —$CD_3$ and —$CH_3$.

In one embodiment of Formula A or Formula I, each of $R^1$, $R^{2a}$, and $R^{1b}$ is independently selected from —$CH_3$ and —$CD_3$; and $R^3$ is selected from —$CH_2$—, and —$CD_2$-.

In still another embodiment of Formula A or Formula I, $R^{2a}$ and $R^{2b}$ are simultaneously —$CD_3$.

In yet another embodiment of Formula A or Formula I, $R^3$ is —$CD_2$-.

According to another embodiment of Formula A or Formula I, $R^4$ is —$CD_2$-$CR^5OH$—$C(R^5)_2$— or —$C(R^5)_2$—$CR^5OH$—$CD_2$-.

According to another embodiment of Formula A or Formula I, $R^4$ is —$CD_2$-$CR^5OH$—$CD_2$-.

According to still another embodiment of Formula A or Formula I, $R^4$ is —$CD_2$-$CDOH$—$CD_2$-.

In another embodiment of Formula A or Formula I, $R^1$, $R^{2a}$, and $R^{2b}$ are simultaneously —$CD_3$.

In another embodiment of Formula A or Formula I, $R^1$ is —$CD_3$; and $R^3$ is —$CD_2$-.

In yet another embodiment of Formula A or Formula I, $R^{2a}$ and $R^{2b}$ are simultaneously —$CD_3$; and $R^3$ is —$CD_2$-.

According to another embodiment of Formula A or Formula I, $R^1$, $R^{2a}$, and $R^{2b}$ are simultaneously —$CD_3$; and $R^3$ is —$CD_2$-.

In one embodiment of Formula A, each Y is the same. In a more specific embodiment, each Y is deuterium.

In still another embodiment, the compound is a compound of Formula A, each Y is the same and the compound is selected from any one of the compounds in Table 1 below.

TABLE 1

Exemplary Compounds of Formula A or pharmaceutically acceptable salts thereof.

| Compound | each Y | $R^1$ | $R^{2a}$ | $R^{2b}$ | $R^3$ | $R^4$ |
|---|---|---|---|---|---|---|
| 100 | H | $CD_3$ | $CH_3$ | $CH_3$ | $CD_2$ | $CH_2CH(OH)CH_2$ |
| 101 | H | $CH_3$ | $CD_3$ | $CD_3$ | $CD_2$ | $CH_2CH(OH)CH_2$ |
| 102 | H | $CD_3$ | $CH_3$ | $CH_3$ | $CH_2$ | $CD_2CD(OH)CD_2$ |
| 103 | H | $CH_3$ | $CD_3$ | $CD_3$ | $CH_2$ | $CD_2CD(OH)CD_2$ |
| 104 | H | $CH_3$ | $CH_3$ | $CH_3$ | $CD_2$ | $CD_2CD(OH)CD_2$ |
| 105 | H | $CD_3$ | $CH_3$ | $CH_3$ | $CD_2$ | $CD_2CD(OH)CD_2$ |
| 106 | H | $CH_3$ | $CD_3$ | $CD_3$ | $CD_2$ | $CD_2CD(OH)CD_2$ |
| 107 | H | $CD_3$ | $CD_3$ | $CD_3$ | $CD_2$ | $CD_2CD(OH)CD_2$ |
| 108 | H | $CD_3$ | $CD_3$ | $CD_3$ | $CH_2$ | $CH_2CH(OH)CH_2$ |
| 109 | H | $CD_3$ | $CH_3$ | $CH_3$ | $CH_2$ | $CH_2CH(OH)CH_2$ |
| 110 | D | $CD_3$ | $CD_3$ | $CD_3$ | $CD_2$ | $CD_2CD(OH)CD_2$ |

According to another set of embodiments, any atom not designated as deuterium in any of the embodiments set forth above is present at its natural isotopic abundance.

The synthesis of compounds of Formula I and Formula A can be readily achieved by synthetic chemists of ordinary skill. Relevant procedures and intermediates are disclosed, for instance in U.S. Pat. No. 4,567,264.

Such methods can be carried out utilizing corresponding deuterated and optionally, other isotope-containing reagents to synthesize the compounds delineated herein, or invoking standard synthetic protocols known in the art for introducing isotopic atoms to a chemical structure.

Exemplary Synthesis

A convenient method for synthesizing compounds of Formula A is depicted in

Scheme 1:

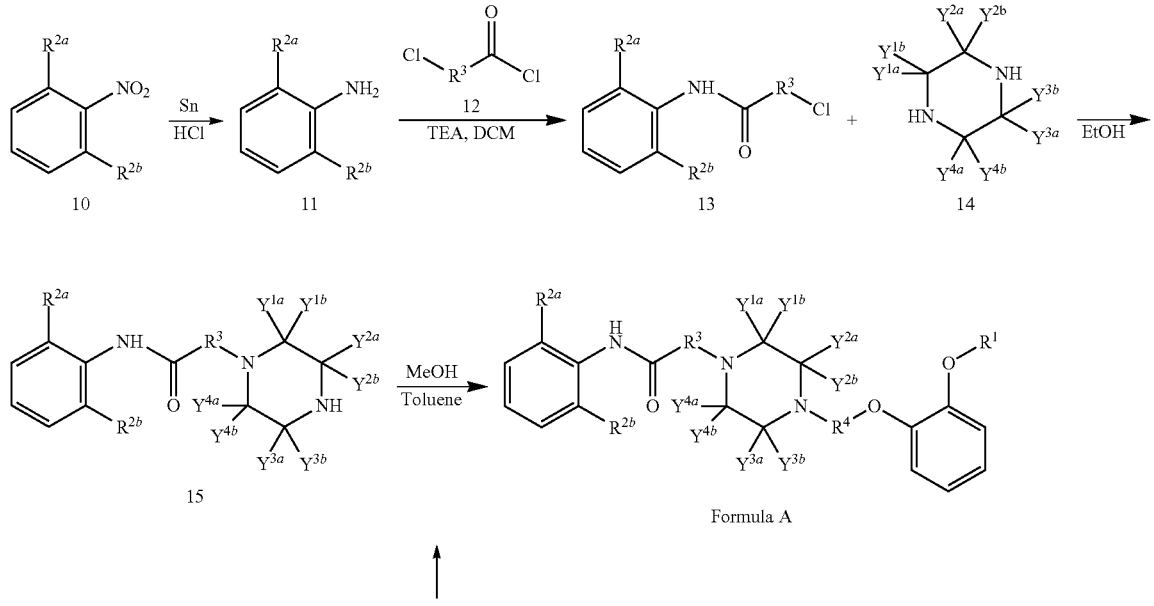

Formula A

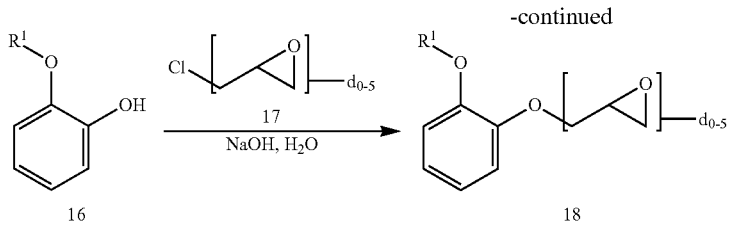

As shown in Scheme 1, deuterated compound 10 is reduced to the aniline with tin and hydrochloric acid (Furniss, B S et al., Vogels Textbook of Practical Organic Chemistry 4$^{th}$ Ed, Longman Scientific, Essex, UK, p. 659). Aniline 11 is then reacted with deuterated acid chloride 12 to provide amide 13. Reaction with deuterated piperazine 14 in refluxing ethanol yields N-alkylated piperazine 15. Deuterated guaiacol 16 is reacted with deuterated epichlorohydrin 17 in aqueous base to provide epoxyether 18 (see Khadidar, B et al., Syn Comm 1997, 27:2051). Reaction of 15 with 18 in refluxing methanol/toluene provides compounds of Formula A.

More particularly, as shown in Scheme 1, commercially available compound 10 ($R^{2a}$=$R^{2b}$=$CD_3$) is reduced to the aniline with tin and hydrochloric acid (Furniss, B S et al., Vogels Textbook of Practical Organic Chemistry 4$^{th}$ Ed, Longman Scientific, Essex, UK, p. 659). The aniline 11 is then reacted with the acid chloride 12 ($R^3$=$CD_2$, prepared from the commercially available acid according to Pellegata, R et al., Synthesis 1985, 5: 517) to provide the amide 13. Reaction with piperazine 14 in refluxing ethanol yields the N-alkylated piperazine 15. The commercially available guaiacol 16 ($R^1$=$CD_3$) is reacted with the commercial epichlorohydrin 17 ($d_5$) in aqueous base to provide the epoxyether 18 (see Khadidar, B et al., Syn Comm 1997, 27:2051). Reaction of 15 with 18 in refluxing methanol/toluene provides compounds of Formula A.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (e.g., $R^1$, $R^2$, $R^3$, $R^4$, etc.) or not. The suitability of a chemical group in a compound structure for use in the synthesis of another compound is within the knowledge of one of ordinary skill in the art.

Additional methods of synthesizing compounds of Formula I and Formula A and their synthetic precursors, including those within routes not explicitly shown in schemes herein, are within the means of chemists of ordinary skill in the art. Synthetic chemistry transformations and protecting group methodologies (protection and deprotection) useful in synthesizing the applicable compounds are known in the art and include, for example, those described in Larock R, *Comprehensive Organic Transformations*, VCH Publishers (1989); Greene T W et al., *Protective Groups in Organic Synthesis,* 3rd Ed., John Wiley and Sons (1999); Fieser L et al., *Fieser and Fieser's Reagents for Organic Synthesis*, John Wiley and Sons (1994); and Paquette L, Ed., *Encyclopedia of Reagents for Organic Synthesis*, John Wiley and Sons (1995) and subsequent editions thereof.

Combinations of substituents and variables envisioned by this invention are only those that result in the formation of stable compounds.

Compositions

The invention also provides pyrogen-free compositions comprising an effective amount of a compound of Formula I or Formula A (e.g., including any of the formulae herein), or a pharmaceutically acceptable salt of the compound; and an acceptable carrier. Preferably, a composition of this invention is formulated for pharmaceutical use ("a pharmaceutical composition"), wherein the carrier is a pharmaceutically acceptable carrier. The carrier(s) must be "acceptable" in the sense of being compatible with the other ingredients of the formulation and, in the case of a pharmaceutically acceptable carrier, not deleterious to the recipient thereof in amounts typically used in medicaments.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, e.g., *Remington's Pharmaceutical Sciences*, Mack Publishing Company, Philadelphia, Pa., 17th Ed. (1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Oral compositions include extended release formulations, such as film-coated extended release tablets. Such extended release formulations can be prepared in a similar manner to extended release formulations of ranolazine, which is described in PCT publications WO2006074398 and WO2001066093, as well as in U.S. Pat. No. 6,303,607, each of which is herein incorporated by reference in its entirety.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g., U.S. Pat. No. 6,803,031.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petrolatum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyl-disiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting the device with the coating composition described above. It will be obvious to those skilled in the art that the coating of the device will occur prior to implantation into a mammal.

According to another embodiment, the invention provides a method of impregnating an implantable drug release device comprising the step of contacting the drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that the compound is therapeutically active.

According to another embodiment, the invention provides an implantable drug release device impregnated with or containing a compound or a composition comprising a compound of this invention, such that the compound is released from the device and is therapeutically active.

Where an organ or tissue is accessible (e.g., because of removal from the patient/subject or surgical procedure) such organ or tissue may be bathed in a medium containing a composition of this invention, a composition of this invention may be painted onto the organ, or a composition of this invention may be applied in any other convenient way.

In another embodiment, a composition of this invention further comprises a second therapeutic agent. The second therapeutic agent may be selected from any compound or therapeutic agent known to have or that demonstrates advantageous properties when administered with a compound having the same mechanism of action as ranolazine. Such agents include those indicated as being useful in combination with ranolazine, including but not limited to, calcium channel blockers; beta-blockers; nitrates; a remodeling agent such as Metoprolol tartate, Enalapril maleate and other agents described in WO200605316; pyridoxal-5'-phosphate and other agents described in WO2006058411; a sterol absorption inhibitor such as those described in WO2002058731; a sodium-hydrogen exchanger type-1 inhibitor such as those described in U.S. Pat. No. 6,423,705; an HMG CoA reductase inhibitor; a UCP inhibitor and/or a Fas antibody such as those described in the WO2005070126; an adenosine A-3 receptor agonist, such as those described in WO2001023399; an aldosterone antagonist, such as eplerenone and others described in WO2002009761; and a quinoline or a derivative or an intermediate thereof as described in WO2001013907.

In anther embodiment, the second therapeutic agent is an agent useful in the treatment or prevention of a disease or condition selected from a cardiovascular disease or condition including, but not limited to, ischemia and damage to the heart and neuronal tissue caused thereby, angina, left ventricular remodeling after heart failure, arrhythmias, congestive heart failure and myocardial infarction; diabetes; obesity; high serum cholesterol; viral infections; endothelial dysfunction; pathological effects of acute increases in free fatty acid flux; inflammatory diseases; proliferative diseases; and wounds.

In one embodiment, the second therapeutic agent is selected from a beta blocker, a calcium channel blocker or a nitrate.

In one embodiment, the second therapeutic agent is the calcium channel blocker amlodipine.

In another embodiment, the second therapeutic agent is the beta blocker atenolol.

In another embodiment, the second therapeutic agent is the nitrate nitroglycerine.

In another embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to treat (therapeutically or prophylactically) the target disorder. For example, and effective amount is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

The interrelationship of dosages for animals and humans (based on milligrams per meter squared of body surface) is described in Freireich et al., Cancer Chemother. Rep. 1966, 50: 219. Body surface area may be approximately determined from height and weight of the patient/subject. See, e.g., *Scientific Tables*, Geigy Pharmaceuticals, Ardsley, N.Y., (1970) 537.

In one embodiment, an effective amount of a compound of this invention for an adult human subject can range from about 1 to 10,000 mg/day. In another embodiment, an effective amount of a compound of this invention for an adult human subject can range from about 100 to 5,000 mg/day. In another embodiment, an effective amount of a compound of this invention for an adult human subject can range from about 100 to 2,000 mg/day.

In a more particular embodiment, an effective amount of a compound of this invention can range from about 5 mg to about 10000 mg per dose, from about 50 mg per dose to about 5000 mg per dose, from about 100 mg to about 2000 mg per dose, or from about 500 mg to about 1000 mg per dose. Dosing can be from 1 to 4 times per day. For example, 1, 2, 3 or 4 times per day. In a particular embodiment, dosing is 2 times per day.

Effective doses will also vary, as recognized by those skilled in the art, depending on the diseases treated, the severity of the disease, the route of administration, the size, sex, age and general health condition of the patient/subject, excipient usage, the possibility of co-usage with other therapeutic treatments such as use of other agents and the judgment of the treating physician. For example, guidance for selecting an effective dose can be determined by reference to the prescribing information for ranolazine.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., Eds., *Pharmacotherapy Handbook*, 2nd Ed., Appleton and Lange, Stamford, Conn. (2000); *PDR Pharmacopoeia, Tarascon Pocket Pharmacopoeia* 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

In another embodiment, the invention provides a method of modulating the activity of fatty acid oxidation in a cell, comprising contacting a cell with one or more compounds of Formula I or Formula A herein.

According to another embodiment, the invention provides a method of treating a disease that is beneficially treated by a partial fatty acid oxidation inhibitor comprising the step of administering to a subject in need thereof an effective amount of a compound or a composition of this invention. Such diseases are well known in the art and include, but are not limited to, a cardiovascular disease or condition including, but not limited to, ischemia and damage to the heart and neuronal tissue caused thereby, angina (both chronic and unstable), arrhythmias, congestive heart failure, myocardial infarction; diabetes; other pathological effects of acute increases in free fatty acid flux; inflammatory diseases; proliferative diseases; and wounds.

In another embodiment, the method of this invention is used to treat a disease or condition in a subject in need thereof selected from chronic angina and unstable angina (acute coronary syndrome).

Methods delineated herein also include those wherein the subject is identified as in need of a particular stated treatment. Identifying a subject in need of such treatment can be in the judgment of a subject or a health care professional and can be subjective (e.g., opinion) or objective (e.g., measurable by a test or diagnostic method).

In another embodiment, any of the above methods of treatment comprises the further step of co-administering to the subject in need thereof one or more second therapeutic agents. The choice of second therapeutic agent may be made from any second therapeutic agent known to be useful for co-administration with ranolazine. Examples of conditions and diseases that may be treated with a compound of this invention (e.g., compounds of Formula I or Formula A) in combination with a second therapeutic agents are: 1) a cardiovascular disease or condition using a calcium channel blocker; a beta-blocker; a nitrate; a remodeling agent such as Metoprolol tartate, Enalapril maleate and other agents described in WO200605316; pyridoxal-5'-phosphate and other agents described in WO2006058411; a sterol absorption inhibitor such as those described in WO2002058731; a sodium-hydrogen exchanger type-1 inhibitor such as those described in U.S. Pat. No. 6,423,705; an aldosterone antagonist, such as eplerenone and others described in WO2002009761; an HMG CoA reductase inhibitor; or an adenosine A-3 receptor agonist, such as those described in WO2001023399 as the second therapeutic agent; 2) diabetes using an HMG CoA reductase inhibitor; a sterol absorption inhibitor such as those described in WO2002058731; or a cholesterol ester transfer protein (CETP) inhibitor; 3) obesity using an HMG CoA reductase inhibitor; a sterol absorption inhibitor such as those described in WO2002058731; or a cholesterol ester transfer protein (CETP) inhibitor; 4) high serum cholesterol using an HMG CoA reductase inhibitor; a sterol absorption inhibitor such as those described in WO2002058731; or a cholesterol ester transfer protein (CETP) inhibitor; 5) viral infections using a quinoline or a derivative or an intermediate thereof as described in WO2001013907; 6) endothelial dysfunction using an HMG CoA reductase inhibitor; 7) inflammatory diseases, proliferative diseases or wound treatment using a UCP inhibitor, or a Fas inhibitor, such as those described in WO2005070126; and 8) proliferative diseases using a chemotherapeutic agent, such as described in WO2004111199.

In particular, the combination therapies of this invention include treatment the chronic angina and unstable angina by administering a compound of Formula I or Formula A and a second therapeutic agent selected from a beta blocker, a calcium channel blocker or a nitrate.

In one embodiment, the second therapeutic agent is the calcium channel blocker amlodipine.

In another embodiment, the second therapeutic agent is the beta blocker atenolol.

In another embodiment, the second therapeutic agent is the nitrate nitroglycerine.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a subject does not preclude the separate administration of that same therapeutic agent, any other second therapeutic agent or any compound of this invention to the subject at another time during a course of treatment.

Effective amounts of these second therapeutic agents are well known to those skilled in the art and guidance for dosing may be found in patents and published patent applications referenced herein, as well as in Wells et al., Eds., *Pharmacotherapy Handbook*, 2nd Ed., Appleton and Lange, Stamford, Conn. (2000); PDR *Pharmacopoeia, Tarascon Pocket Pharmacopoeia* 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In another embodiment, this invention provides for the use of a compound of Formula I or Formula A, alone or together with one of the above-described second therapeutic agents, in the manufacture of a medicament, either in a single composition or in separate dosage forms, for treating a disease that is beneficially treated by ranolazine. Such diseases are well known in the art and are set forth above. In one embodiment, the disease is selected from chronic angina and unstable angina.

Diagnostic Methods and Kits

The compounds and compositions of this invention are also useful as reagents in methods for determining the concentration of ranolazine in solution, examining the metabolism of ranolazine and other analytical studies. Additional utility of compounds of any of the formulas herein include their use as internal standards to determine the true concentration(s) of corresponding non-deuterated compounds (e.g., ranolazine) in biological matrices, such as plasma.

According to one embodiment, the invention provides a method of determining the concentration, in a biological sample of a non-deuterated compound corresponding to a compound of Formula I or Formula A, comprising the steps of:

a) adding a known concentration of the compound of Formula I or A, to the biological sample;

b) subjecting the biological sample to a measuring device that distinguishes the non-deuterated compound from a compound of Formula I or A;

c) calibrating the measuring device to correlate the detected quantity of the compound of Formula I or A with the known concentration of the compound of Formula I or A added to the biological sample; and d) determining the concentration of the non-deuterated compound in the biological sample by comparing the detected quantity of the non-deuterated compound with the detected quantity and known concentration of the corresponding compound of Formula I or A.

Measuring devices that can distinguish the non-deuterated compound from the corresponding compound(s) of Formula I or A include any measuring device that can distinguish between compounds that are of identical structure except that one contains one or more deuterium atoms in place of one or more hydrogen atoms, or one or more $^{13}C$ atoms in place of one or more $^{12}C$ atoms. Exemplary measuring devices include a mass spectrometer, NMR spectrometer, or IR spectrometer.

In another embodiment, the invention provides a method of evaluating the metabolic stability of a compound of Formula I or A comprising the steps of contacting the compound of Formula I or A with a metabolizing enzyme source for a period of time and comparing the amount of the compound with the metabolic products of the compound after the period of time.

The present invention also provides kits for use to treat chronic angina or unstable angina. These kits comprise (a) a pharmaceutical composition comprising a compound of Formula I or A or a salt thereof, wherein the pharmaceutical composition is in a container; and (b) instructions describing a method of using the pharmaceutical composition to treat chronic angina or unstable angina.

The container may be any vessel or other sealed or sealable apparatus that can hold the pharmaceutical composition. Examples include bottles, ampules, divided or multi-chambered holders bottles, wherein each division or chamber comprises a single dose of the composition, a divided foil packet wherein each division comprises a single dose of the composition, or a dispenser that dispenses single doses of the composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. In on embodiment, the container is a blister pack.

The kit may additionally comprise a memory aid of the type containing information and/or instructions for the physician, pharmacist or subject. Such memory aids include numbers printed on each chamber or division containing a dosage that corresponds with the days of the regimen which the tablets or capsules so specified should be ingested, or days of the week printed on each chamber or division, or a card which contains the same type of information. For single dose dispensers, memory aids further include a mechanical counter which indicates the number of daily doses that have been dispensed and a battery-powered micro-chip memory coupled with a liquid crystal readout and/or audible reminder signal which, for example, reads out the date that the last daily dose has been taken and/or reminds one when the next dose is to be taken. Other memory aids useful in such kits are a calendar printed on a card, as well as other variations that will be readily apparent.

The kits of this invention may also comprise a device to administer or to measure out a unit dose of the pharmaceutical composition. Such device may include an inhaler if the composition is an inhalable composition; a syringe and needle if the composition is an injectable composition; a syringe, spoon, pump, or a vessel with or without volume markings if the composition is an oral liquid composition; or any other measuring or delivery device appropriate to the dosage formulation of the composition present in the kit.

In certain embodiment, the kits of this invention may comprise in a separate vessel of container a pharmaceutical composition comprising a second therapeutic agent, such as one of those listed above for use for co-administration with a compound of this invention.

EXAMPLES

Example 1

Synthesis of intermediate 2-((2-d$_3$-methoxyphenoxy)-d$_2$-methyl)-d$_3$-oxirane (22)

Intermediate 22 was prepared according to Scheme 2, below. Details of the synthesis are set forth below.

Scheme 2. Preparation of Intermediate 2-((2-d$_3$-methoxyphenoxy)-d$_2$-methyl)-d$_3$-oxirane.

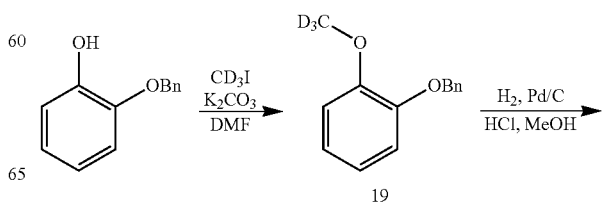

19

-continued

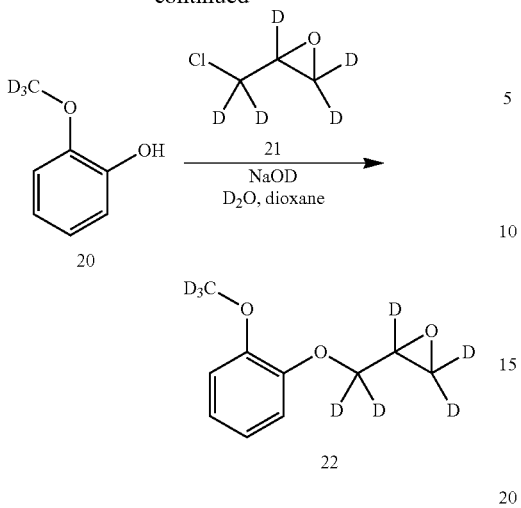

Synthesis of 1-(benzyloxy)-2-$d_3$-methoxybenzene (19). Iodomethane-$d_3$ (25 g, 172 mmol) was added to a solution of 2-(benzyloxy)phenol (25 g, 125 mmol) in 500 mL DMF followed by potassium carbonate (19 g, 137 mmol). The mixture was stirred at 80° C. for 2 h. The solid was removed by filtration and washed with ethyl acetate (200 mL). The organic filtrate was washed sequentially with saturated sodium bicarbonate and brine, dried over $Na_2SO_4$, filtered and concentrated under reduced pressure to give a yellow solid. The crude product was purified by chromatography on silica gel (20% ethyl acetate/heptanes) to give 27.8 g (102%) of 19 as a white solid.

Synthesis of 2-$d_3$-methoxyphenol (20). Compound 19 (27 g, 124 mmol) was dissolved in a mixture of 2N hydrochloric acid (15 mL) and methanol (300 mL) under $N_2$ and 10% Pd—C (6 g) was added. The mixture was hydrogenated at 40 psi $H_2$ for 6 h. The mixture was filtered through a celite pad, and the pad was washed with methanol (50 mL). The filtrate was concentrated under reduced pressure and the residue was diluted with dichloromethane (300 mL). The solution was washed with 1N hydrochloric acid and with brine, dried over $Na_2SO_4$, filtered and concentrated under reduced pressure to give 14.5 g (91.9%) of compound 20 as a light yellow oil.

Synthesis of 2-((2-$d_3$-methoxyphenoxy)-$d_2$-methyl)-$d_3$-oxirane (22). Epichlorohydrin-$d_5$ 21 (6 g, 61.5 mmol) was added to a solution of 7.8 g of compound 20 (61.3 mmol) in dioxane (60 mL) followed by 40% NaOD in $D_2O$ (4.4 mL, 64.6 mmol). The mixture was stirred under reflux conditions for 4 h, then cooled to room temperature and diluted with ethyl acetate (60 mL). The aqueous layer was further extracted with ethyl acetate (20 mL). The combined organic solution was washed with brine, dried over $Na_2SO_4$, filtered, and concentrated under reduced pressure. The crude product was chromatographed on silica gel (25% ethyl acetate/heptanes) to give 7 g (58%) of compound 22 as a pink oil.

Example 2

Synthesis of N-(2,6-di($d_3$-methyl)phenyl)-2-(4-(2-hydroxy-3-(2-$d_3$-(methoxy)phenoxy)-$d_5$-propyl)-$d_8$-piperazin-1-yl)-2,2-$d_2$-acetamide (Compound 110)

Compound 110 was prepared according to Scheme 3, below. The details of each step in the synthesis are set forth below as General Method A.

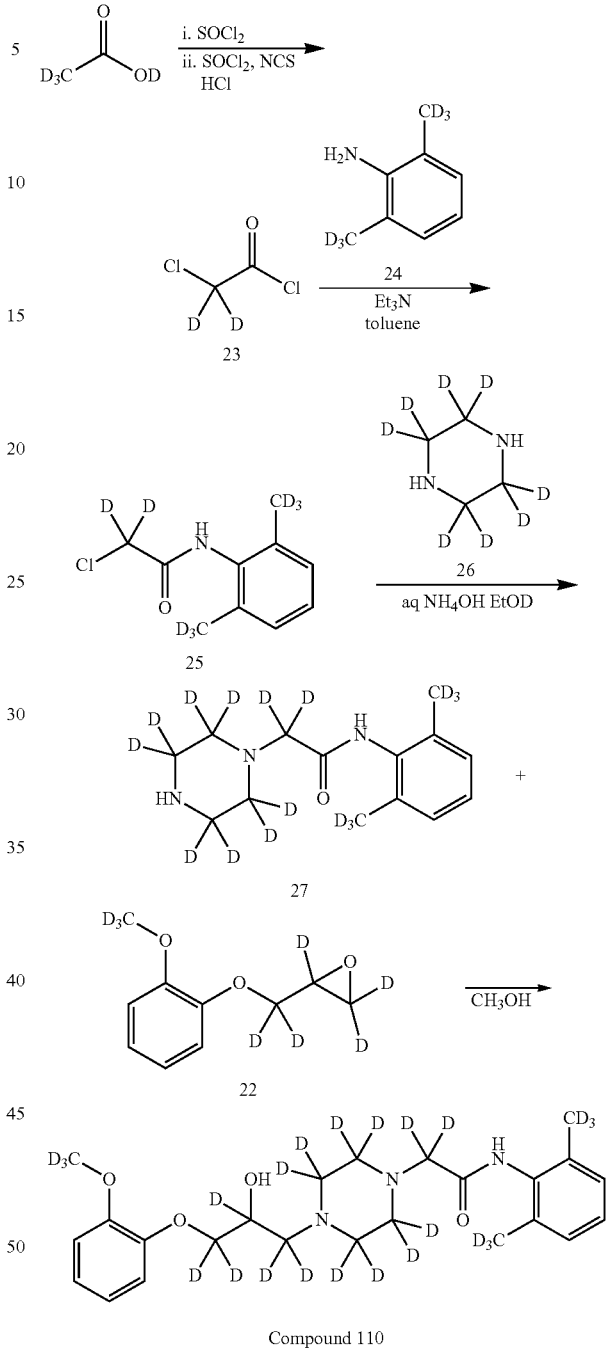

Compound 110

Synthesis of 2-$d_2$-chloroacetyl chloride (23). A solution of acetic acid-$d_4$ (6.4 mL, 133.2 mmol) in thionyl chloride (40 mL, 535 mmol) was stirred at 70° C. for 30 min, then cooled to room temperature. N-Chlorosuccinimide (36.6 g, 266 mmol), thionyl chloride (27 mL, 370 mmol) and concentrated hydrochloric acid (7 drops) were added. The mixture was refluxed for 2 hr at 90° C. Most of the thionyl chloride was removed by careful distillation under reduced pressure. The pot residue was filtered, washing the solid with carbon tetrachloride (50 mL). The filtrate was carefully distilled to give 8 g (60%) of 23 as a clear liquid, bp 100-105° C. (760 mm Hg).

Synthesis of 2-Chloro-N-(2,6-di($d_3$-methyl)phenyl)-2,2-$d_2$-acetamide (25). Triethyl amine (4.61 mL, 32.8 mmol) was added to a solution of 2,6-di($d_3$-methyl)aniline 24 (3.5 g, 27.3 mmol) in toluene (50 mL) at 0° C. and compound 23 (3.14 g, 27.3 mmol) was added. The mixture was warmed to room temperature and stirred for 2 h. The mixture was quenched with 2N hydrochloric acid (20 mL), and extracted with ethyl acetate (60 mL). The organic layer was washed with brine, dried over $Na_2SO_4$, filtered, and concentrated under reduced pressure. The crude product was triturated with hexanes to give 4.2 g (75%) of 25 as an off-white solid.

Synthesis of N-(2,6-di($d_3$-methyl)phenyl)-2-($d_8$-piperazin-1-yl)-2,2-$d_2$-acetamide (27). Compound 25 (600 mg, 2.67 mmol) was added to a solution of piperazine-$d_8$ (1 g, 10.64 mmol) in ethanol-$d_1$ (20 mL) The mixture was stirred under reflux conditions for 3 h, cooled to room temperature, and ammonium hydroxide (3.8 mL) was added. The mixture was concentrated under reduced pressure distillation. The residue was diluted with dichloromethane (80 mL) and the solution washed with brine, dried over $Na_2SO_4$, filtered and concentrated under reduced pressure. The crude product was triturated with MTBE to give 700 mg (99%) of compound 27 as a gray solid.

Synthesis of N-(2,6-di($d_3$-methyl)phenyl)-2-(4-(2-hydroxy-3-(2-$d_3$-(methoxy)phenoxy)-$d_5$-propyl)-$d_8$-piperazin-1-yl)-2,2-$d_2$-acetamide (Compound 110). Compound 22 (454 mg, 2.42 mmol) was added to a solution of compound 27 (700 mg, 2.66 mmol) in methanol (30 mL). The reaction was stirred under reflux conditions for 5 h and concentrated under reduced pressure to give a dark-brown oil. The crude product was diluted with ethanol (~200 mL), decolorized with activated carbon (4 g), then purified by chromatography on silica gel (100% ethyl acetate followed by 0-10% methanol/dichloromethane) to give 540 mg (50%) of Compound 110 as a light brown solid. $^1$H-NMR (300 MHz, $CDCl_3$): δ 6.87-6.99 (m, 4H), 7.09-7.11 (m, 3H), 8.65 (s, 1H). $^{13}$C-NMR (75 MHz, $CDCl_3$): δ 111.92, 114.75, 120.88, 121.94, 127.19, 128.31, 133.64, 134.82, 148.22, 149.82, 168.41. HPLC 99.8% purity (method: 20 mm C18-RP column—gradient method 2-95% ACN+0.1% formic acid in 3.3 min with 1.7 min hold at 95% ACN; Wavelength: 210 nm): retention time: 2.51 min. MS (M+H$^+$): 452.4.

Example 3

Synthesis of N-(2,6-dimethylphenyl)-2-(4-(2-hydroxy-3-(2-$d_3$-(methoxy)phenoxy)propyl)piperazin-1-yl)-2,2-$d_2$-acetamide (Compound 100)

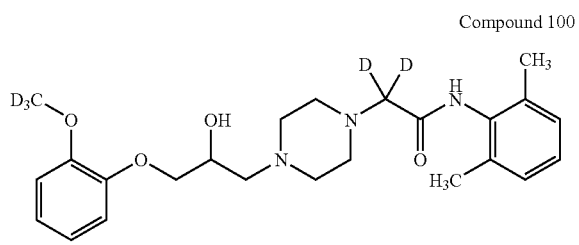

Compound 100

Compound 100 was prepared according to Schemes 1 and 3, above, utilizing deuterated reagents, and following the General Method A described above.

Synthesis of N-(2,6-dimethylphenyl)-2-(4-(2-hydroxy-3-(2-$d_3$-(methoxy)phenoxy)propyl)piperazin-1-yl)-2,2-$d_2$-acetamide (Compound 100). Compound 100 was prepared via General Method A, above, from 2-((2-$d_3$-methoxyphenoxy)methyl)oxirane (18, where $R^1$=$CD_3$; prepared according to Schemes 1 and 2 using deuterated reagents) and N-(2,6-di(methyl)phenyl)-2-(piperazin-1-yl)-2,2-$d_2$-acetamide (15, where $R^{2a}$, $R^{2b}$=$CH_3$, $R^3$=$CD_2$, and all Y=H; prepared according to Schemes 1 and 3 using deuterated reagents). $^1$H-NMR (300 MHz, $CDCl_3$): δ 2.23 (s, 6H), 2.56-2.65 (m, 4H), 2.74 (br s, 6H), 4.03-4.05 (m, 2H), 4.11-4.19 (m, 1H), 6.87-6.99 (m, 4H), 7.06-7.13 (m, 3H), 8.65 (s, 1H). $^{13}$C-NMR (75 MHz, $CDCl_3$): δ 18.91, 53.80, 54.02, 60.76, 66.18, 72.53, 112.15, 115.01, 121.12, 122.20, 127.44, 128.55, 133.82, 135.19, 148.47, 150.07, 168.63. HPLC 99.7% purity (method: 20 mm C18-RP column—gradient method 2-95% ACN+0.1% formic acid in 3.3 min with 1.7 min hold at 95% ACN; Wavelength: 210 nm): retention time: 2.52 min. MS (M+H$^+$): 433.2.

Example 4

Synthesis of N-(2,6-dimethylphenyl)-2-(4-(2-hydroxy-3-(2-$d_3$-(methoxy)phenoxy)-$d_5$-propyl)piperazin-1-yl)acetamide (Compound 102)

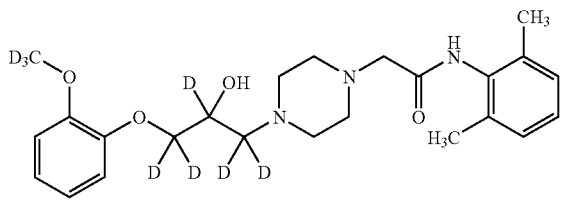

Compound 102

Compound 102 was prepared according to Schemes 1 and 3, above, utilizing deuterated reagents, and following the General Method A described above.

Synthesis of N-(2,6-dimethylphenyl)-2-(4-(2-hydroxy-3-(2-$d_3$-(methoxy)phenoxy)-$d_5$-propyl)piperazin-1-yl)acetamide (Compound 102). Compound 102 was prepared via General Method A, above, from 2-((2-$d_3$-methoxyphenoxy)-$d_2$-methyl)-$d_3$-oxirane (18, where $R^1$=$CD_3$; prepared according to Schemes 1 and 2 using deuterated reagents) and N-(2,6-di(methyl)phenyl)-2-(piperazin-1-yl)acetamide (15, where $R^{2a}$, $R^{2b}$=$CH_3$, $R^3$=$CH_2$, and all Y=H; prepared according to Schemes 1 and 3 using deuterated reagents). $^1$H-NMR (300 MHz, $CDCl_3$): δ 2.23 (s, 6H), 2.59 (br s, 2H), 2.75 (br s, 6H), 3.21 (s, 2H), 6.87-6.99 (m, 4H), 7.06-7.14 (m, 3H), 8.64 (s, 1H). $^{13}$C-NMR (75 MHz, $CDCl_3$): δ 18.65, 53.49, 53.83, 61.64, 111.92, 114.77, 120.88, 121.95, 127.20, 128.30, 133.58, 134.95, 148.22, 149.83, 168.36. HPLC 99.8% purity (method: 20 mm C18-RP column—gradient method 2-95% ACN+0.1% formic acid in 3.3 min with 1.7

Example 5

Synthesis of N-(2,6-dimethylphenyl)-2-(4-(2-hydroxy-3-(2-d₃-(methoxy)phenoxy)-d₅-propyl)piperazin-1-yl)-2,2-d₂-acetamide (Compound 105)

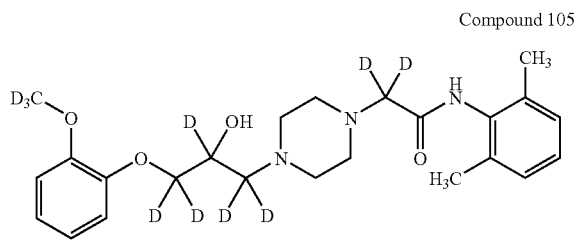

Compound 105

Compound 105 was prepared according to Schemes 1 and 3, above, utilizing deuterated reagents, and following the General Method A described above.

Synthesis of N-(2,6-dimethylphenyl)-2-(4-(2-hydroxy-3-(2-d₃-(methoxy)phenoxy)-d₅-propyl)piperazin-1-yl)-2,2-d₂-acetamide (Compound 105). Compound 105 was prepared via General Method A, above, from 2-((2-d₃-methoxyphenoxy)-d₂-methyl)-d₃-oxirane (18, where $R^1$=CD₃; prepared according to Schemes 1 and 2 using deuterated reagents) and N-(2,6-di(methyl)phenyl)-2-(piperazin-1-yl)-2,2-d₂-acetamide (15, where $R^{2a}$, $R^{2b}$=CH₃, $R^3$=CD₂, and all Y=H; prepared according to Schemes 1 and 3 using y deuterated reagents). ¹H-NMR (300 MHz, CDCl₃): δ 2.23 (s, 6H), 2.58 (br s, 2H), 2.74 (bs, 6H), 6.87-6.99 (m, 4H), 7.06-7.14 (m, 3H), 8.65 (s, 1H). ¹³C-NMR (75 MHz, CDCl₃): δ 18.90, 53.74, 54.03, 112.16, 114.99, 121.13, 122.17, 127.43, 128.54, 133.83, 135.19, 148.48, 150.07, 168.63. HPLC 99.5% purity (method: 20 mm C18-RP column—gradient method 2-95% ACN+0.1% formic acid in 3.3 min with 1.7 min hold at 95% ACN; Wavelength: 210 nm): retention time: 2.52 min. MS (M+H⁺): 438.3.

Example 6

Synthesis of N-(2,6-di(d₃-methyl)phenyl)-2-(4-(2-hydroxy-3-(2-d₃-(methoxy)phenoxy)-d₅-propyl)piperazin-1-yl)-2,2-d₂-acetamide (Compound 107)

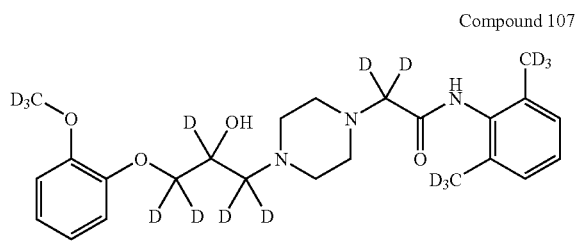

Compound 107

Compound 107 was prepared according to Schemes 1 and 3, above, utilizing deuterated reagents, and following the General Method A described above.

Synthesis of N-(2,6-di(d₃-methyl)phenyl)-2-(4-(2-hydroxy-3-(2-d₃-(methoxy)phenoxy)-d₅-propyl)piperazin-1-yl)-2,2-d₂-acetamide (Compound 107). Compound 107 was prepared via General Method A, above, from 2-((2-d₃-methoxyphenoxy)-d₂-methyl)-d₃-oxirane (18, where $R^1$=CD₃; prepared according to Schemes 1 and 2 using deuterated reagents) and N-(2,6-di(d₃-methyl)phenyl)-2-(piperazin-1-yl)-2,2-d₂-acetamide (15, where $R^{2a}$, $R^{2b}$=CD₃, $R^3$=CD₂, and all Y=H; prepared according to Schemes 1 and 3 using deuterated reagents). ¹H-NMR (300 MHz, CDCl₃): δ 2.59 (br s, 2H), 2.75 (br s, 6H), 6.87-6.99 (m, 4H), 7.06-7.13 (m, 3H), 8.65 (s, 1H). ¹³C-NMR (75 MHz, CDCl₃): δ 53.48, 53.75, 55.78, 111.92, 114.75, 120.87, 121.93, 127.17, 128.29, 133.63, 134.81, 148.22, 149.82, 168.37. HPLC 99.8% purity (method: 20 mm C18-RP column—gradient method 2-95% ACN+0.1% formic acid in 3.3 min with 1.7 min hold at 95% ACN; Wavelength: 210 nm): retention time: 2.51 min. MS (M+H⁺): 444.3.

Example 7

Synthesis of N-(2,6-di(d₃-methyl)phenyl)-2-(4-(2-hydroxy-3-(2-d₃-(methoxy)phenoxy)propyl)piperazin-1-yl)acetamide (Compound 108)

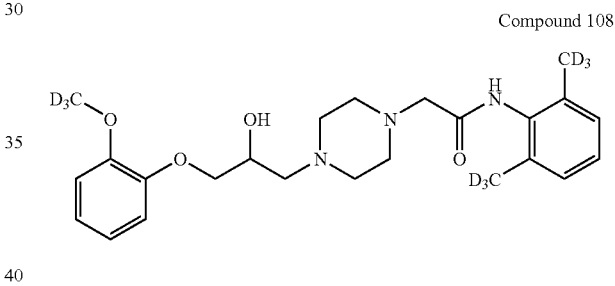

Compound 108

Compound 108 was prepared according to Schemes 1 and 3, above, utilizing deuterated reagents, and following the General Method A described above.

Synthesis of N-(2,6-di(d₃-methyl)phenyl)-2-(4-(2-hydroxy-3-(2-d₃-(methoxy)phenoxy)propyl)piperazin-1-yl)acetamide-(Compound 108). Compound 108 was prepared via General Method A, above, from 2-((2-d₃-methoxyphenoxy)methyl)oxirane (18, where $R^1$=CD₃; prepared according to Schemes 1 and 2 using deuterated reagents) and N-(2,6-di(d₃-methyl)phenyl)-2-(piperazin-1-yl)acetamide (15, where $R^{2a}$, $R^{2b}$=CD₃, $R^3$=CH₂, and all Y=H; prepared according to Schemes 1 and 3 using deuterated reagents). ¹H-NMR (300 MHz, CDCl₃): δ 2.54-2.65 (m, 4H), 2.74 (br s, 6H), 3.20 (s, 2H), 3.43 (br s, 1H), 4.03-4.05 (m, 2H), 4.11-4.19 (m, 1H), 6.87-6.99 (m, 4H), 7.06-7.14 (m, 3H), 8.64 (s, 1H). ¹³C-NMR (75 MHz, CDCl₃): δ 53.80, 54.05, 60.77, 61.87, 66.20, 72.53, 112.16, 115.00, 121.13, 122.20, 127.43, 128.55, 133.89, 135.07, 148.47, 150.07, 168.62. HPLC 99.7% purity (method: 20 mm C18-RP column—gradient method 2-95% ACN+0.1% formic acid in 3.3 min with 1.7 min hold at 95% ACN; Wavelength: 210 nm): retention time: 2.50 min. MS (M+H⁺): 437.4.

Example 8

Synthesis of N-(2,6-dimethylphenyl)-2-(4-(2-hydroxy-3-(2-d₃-(methoxy)phenoxy)propyl)piperazin-1-yl)acetamide (Compound 109)

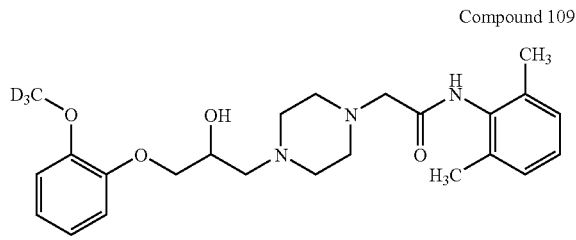

Compound 109

Compound 109 was prepared according to Schemes 1 and 3, above, utilizing deuterated reagents, and following the General Method A described above.

Synthesis of N-(2,6-dimethylphenyl)-2-(4-(2-hydroxy-3-(2-d₃-(methoxy)phenoxy)propyl)piperazin-1-yl)acetamide (Compound 109). Compound 109 was prepared via General Method A, above, from 2-((2-d₃-methoxyphenoxy)methyl) oxirane (18, where $R^1$=$CD_3$; prepared according to Schemes 1 and 2 using deuterated reagents) and N-(2,6-di(methyl)phenyl)-2-(piperazin-1-yl)acetamide (15, where $R^{2a}$, $R^{2b}$=$CH_3$, $R^3$=$CH_2$, and all Y=H; prepared according to Schemes 1 and 3 using deuterated reagents). $^1$H-NMR (300 MHz, CDCl₃): δ 2.23 (s, 6H), 2.57-2.62 (m, 4H), 2.75 (br s, 6H), 3.22 (s, 2H), 4.04-4.05 (m, 2H), 4.14-4.18 (m, 1H), 6.87-7.00 (m, 4H), 7.08-7.11 (m, 3H), 8.65 (s, 1H). $^{13}$C-NMR (75 MHz, CDCl₃): δ 18.65, 53.55, 53.82, 60.52, 61.63, 65.94, 72.28, 111.92, 114.78, 120.88, 121.97, 127.20, 128.30, 133.57, 134.95, 148.22, 149.83, 168.36. HPLC 99.7% purity (method: 20 mm C18-RP column—gradient method 2-95% ACN+0.1% formic acid in 3.3 min with 1.7 min hold at 95% ACN; Wavelength: 210 nm): retention time: 2.49 min. MS (M+H⁺): 431.4.

Evaluation of Compound Stability

Certain in vitro liver metabolism studies have been described previously in the following references, each of which is incorporated herein in their entirety: Obach R S, Drug Metab. Disp. 1999, 27: 1350; Houston, J B et al., Drug Metab. Rev. 1997, 29: 891; Houston J B Biochem Pharmacol 1994, 47: 1469; Iwatsubo T et al., Pharmacol. Ther. 1997, 73: 147; and Lave T. et al., Pharm. Res. 1997, 14: 152.

Microsomal Assay: The metabolic stability of compounds of Formula I or Formula A is tested using pooled liver microsomal incubations. Full scan LC-MS analysis is then performed to detect major metabolites. Samples of the test compounds, exposed to pooled human liver microsomes, are analyzed using HPLC-MS (or MS/MS) detection. For determining metabolic stability, multiple reaction monitoring (MRM) is used to measure the disappearance of the test compounds. For metabolite detection, Q1 full scans are used as survey scans to detect the major metabolites.

[1] Experimental Procedures: Human liver microsomes are obtained from a commercial source (e.g., Absorption Systems L. P. (Exton, Pa.) or XenoTech, LLC (Lenexa, Kans.)). The incubation mixtures are prepared as follows:

Reaction Mixture Composition

| | |
|---|---|
| Liver Microsomes | 0.5-2.0 mg/mL |
| NADPH | 1 mM |
| Potassium Phosphate, pH 7.4 | 100 mM |
| Magnesium Chloride | 10 mM |
| Test Compound | 0.1-1 μM. |

Incubation of Test Compounds with Liver Microsomes: The reaction mixture, minus cofactors, is prepared. An aliquot of the reaction mixture (without cofactors) is incubated in a shaking water bath at 37° C. for 3 minutes. Another aliquot of the reaction mixture is prepared as the negative control. The test compound is added into both the reaction mixture and the negative control at a final concentration of 1 μM. An aliquot of the reaction mixture is prepared as a blank control, by the addition of plain organic solvent (not the test compound). The reaction is initiated by the addition of cofactors (not into the negative controls), and then incubated in a shaking water bath at 37° C. Aliquots (200 μL) are withdrawn in triplicate at multiple time points (e.g., 0, 15, 30, 60, and 120 minutes) and combined with 800 μL of ice-cold 50/50 acetonitrile/dH₂O to terminate the reaction. The positive controls, testosterone and propranolol, as well as ranolazine, are each run simultaneously with the test compounds in separate reactions.

All samples are analyzed using LC-MS (or MS/MS). An LC-MRM-MS/MS method is used for metabolic stability. Also, Q1 full scan LC-MS methods are performed on the blank matrix and the test compound incubation samples. The Q1 scans serve as survey scans to identify any sample unique peaks that might represent the possible metabolites. The masses of these potential metabolites can be determined from the Q1 scans.

SUPERSOMES™ Assay. Various human cytochrome P450-specific SUPERSOMES™ are purchased from Gentest (Woburn, Mass., USA). A 1.0 mL reaction mixture containing 25 pmole of SUPERSOMES™, 2.0 mM NADPH, 3.0 mM MgCl, and 1 μM of a compound of test in 1100 mM potassium phosphate buffer (pH 7.4) is incubated at 37° C. in triplicate. Positive controls contain 1 μM of ranolazine instead of a test compound. Negative controls used Control Insect Cell Cytosol (insect cell microsomes that lacked any human metabolic enzyme) purchased from GenTest (Woburn, Mass., USA). Aliquots (50 μL) are removed from each sample and placed in wells of a multi-well plate at various time points (e.g., 0, 2, 5, 7, 12, 20, and 30 minutes) and to each aliquot is added 50 μL of ice cold acetonitrile with 3 μM haloperidol as an internal standard to stop the reaction.

Plates containing the removed aliquots are placed in −20° C. freezer for 15 minutes to cool. After cooling, 100 μL of deionized water is added to all wells in the plate. Plates are then spun in the centrifuge for 10 minutes at 3000 rpm. A portion of the supernatant (100 μL) is then removed, placed in a new plate and analyzed using Mass Spectrometry.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference.

What is claimed is:

1. A compound of Formula A:

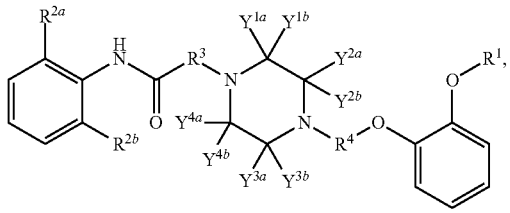

or a pharmaceutically acceptable salt thereof wherein:
R$^1$ is —CD$_3$;
each of R$^{2a}$ and R$^{2b}$ is independently selected from —CH$_3$, and —CD$_3$;
R$^3$ is selected from —CH$_2$ and —CD$_2$-;
R$^4$ is —C(R$^5$)$_2$—CR$^5$OH—C(R$^5$)$_2$—, wherein each R$^5$ is independently selected from D and H; and
each Y is independently selected from H and D.

2. The compound of claim 1, wherein each Y is the same.

3. The compound of claim 2, wherein each Y is deuterium.

4. The compound of claim 2 wherein: each Y is hydrogen.

5. The compound according to claim 1, wherein the compound is selected from any one of the compounds in the table below or a pharmaceutically acceptable salt thereof:

| Compound | each Y | R$^1$ | R$^{2a}$ | R$^{2b}$ | R$^3$ | R$^4$ |
|---|---|---|---|---|---|---|
| 100 | H | CD$_3$ | CH$_3$ | CH$_3$ | CD$_2$ | CH$_2$CH(OH)CH$_2$ |
| 102 | H | CD$_3$ | CH$_3$ | CH$_3$ | CH$_2$ | CD$_2$CD(OH)CD$_2$ |
| 105 | H | CD$_3$ | CH$_3$ | CH$_3$ | CD$_2$ | CD$_2$CD(OH)CD$_2$ |
| 107 | H | CD$_3$ | CD$_3$ | CD$_3$ | CD$_2$ | CD$_2$CD(OH)CD$_2$. |

6. The compound according to claim 1, wherein the compound is selected from any one of the compounds in the table below or a pharmaceutically acceptable salt thereof:

| Compound | each Y | R$^1$ | R$^{2a}$ | R$^{2b}$ | R$^3$ | R$^4$ |
|---|---|---|---|---|---|---|
| 108 | H | CD$_3$ | CD$_3$ | CD$_3$ | CH$_2$ | CH$_2$CH(OH)CH$_2$ |
| 109 | H | CD$_3$ | CH$_3$ | CH$_3$ | CH$_2$ | CH$_2$CH(OH)CH$_2$ |
| 110 | D | CD$_3$ | CD$_3$ | CD$_3$ | CD$_2$ | CD$_2$CD(OH)CD$_2$. |

7. The compound according to any one of claims 1 to 4 and 5 to 6, wherein any atom not designated as deuterium is present at its natural isotopic abundance.

8. A pyrogen-free composition comprising an effective amount of a compound of Formula A:

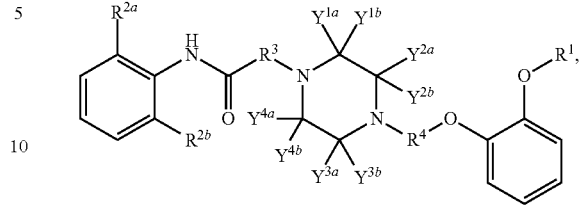

or a pharmaceutically acceptable salt thereof wherein:
R$^1$ is —CD$_3$;
each of R$^{2a}$ and R$^{2b}$ is independently selected from —CH$_3$ and —CD$_3$;
R$^3$ is selected from —CH$_2$ and —CD$_2$-;
R$^4$ is —C(R$^5$)$_2$—CR$^5$OH—C(R$^5$)$_2$—, wherein each R$^5$ is independently selected from D and H; and
each Y is independently selected from H and D;
and an acceptable carrier.

9. The composition according to claim 8, wherein the composition is formulated for pharmaceutical use; and the carrier is a pharmaceutically acceptable carrier.

10. The composition according to claim 9, further comprising a second therapeutic agent useful in treating a subject suffering from or susceptible to a disease or condition selected from ischemia; angina; left ventricular remodeling after heart failure; arrhythmias; congestive heart failure; myocardial infarction; diabetes; obesity; high serum cholesterol; viral infections; endothelial dysfunction; pathological effects of acute increases in free fatty acid flux; inflammatory diseases; proliferative diseases; and wounds.

11. The composition according to claim 10, wherein the second therapeutic agent is selected from a calcium channel blocker; a beta-blocker; a nitrate; a remodeling agent; a sterol absorption inhibitor; a sodium-hydrogen exchanger type-1 inhibitor; an HMG CoA reductase inhibitor; a UCP inhibitor; a Fas inhibitor; an adenosine A-3 receptor agonist; an aldosterone antagonist; and a quinoline or a derivative or an intermediate thereof.

12. The composition according to claim 11, wherein the second therapeutic agent is selected from a beta blocker, a calcium channel blocker or a nitrate.

13. The composition according to claim 12, wherein the second therapeutic agent is amlodipine, atenolol, or nitroglycerine.

14. The compound of claim 1, wherein R$^{2a}$ and R$^{2b}$ are simultaneously —CD$_3$ or —CH$_3$.

15. The compound of claim 14, wherein R$^{2a}$ and R$^{2b}$ are simultaneously —CD$_3$.

16. The compound of claim 15, wherein R$^3$ is —CD$_2$-.

17. The compound of claim 16, wherein R$^4$ is —CD$_2$-CR$^5$OH—C(R$^5$)$_2$— or —C(R$^5$)$_2$—CR$^5$OH—CD$_2$-.

18. The compound of claim 17, wherein R$^4$ is —CD$_2$-CR$^5$OH—CD$_2$-.

19. The compound of claim 18, wherein R$^4$ is —CD$_2$-CDOH—CD$_2$-.

20. The compound of claim 4, wherein R$^{2a}$ and R$^{2b}$ are simultaneously —CD$_3$ or —CH$_3$.

21. The compound of claim 20, wherein R$^{2a}$ and R$^{2b}$ are simultaneously —CD$_3$.

22. The compound of claim 21, wherein R$^3$ is —CD$_2$-.

23. The compound of claim 22, wherein R$^4$ is —CD$_2$-CR$^5$OH—C(R$^5$)$_2$— or —C(R$^5$)$_2$—CR$^5$OH—CD$_2$-.

24. The compound of claim 23, wherein R$^4$ is —CD$_2$-CR$^5$OH—CD$_2$-.

25. The compound of claim 24, wherein $R^4$ is —$CD_2$-CDOH—$CD_2$-.

26. A pyrogen-free composition comprising an effective amount of a compound of claim 4 or a pharmaceutically acceptable salt thereof, and an acceptable carrier.

27. The composition according to claim 26, wherein the composition is formulated for pharmaceutical use; and the carrier is a pharmaceutically acceptable carrier.

28. The composition according to claim 27, further comprising a second therapeutic agent useful in treating a subject suffering from or susceptible to a disease or condition selected from ischemia; angina; left ventricular remodeling after heart failure; arrhythmias; congestive heart failure; myocardial infarction; diabetes; obesity; high serum cholesterol; viral infections; endothelial dysfunction; pathological effects of acute increases in free fatty acid flux; inflammatory diseases; proliferative diseases; and wounds.

29. The composition according to claim 28, wherein the second therapeutic agent is selected from a calcium channel blocker; a beta-blocker; a nitrate; a remodeling agent; a sterol absorption inhibitor; a sodium-hydrogen exchanger type-1 inhibitor; an HMG CoA reductase inhibitor; a UCP inhibitor; a Fas inhibitor; an adenosine A-3 receptor agonist; an aldosterone antagonist; and a quinoline or a derivative or an intermediate thereof.

30. The composition according to claim 29, wherein the second therapeutic agent is selected from a beta blocker, a calcium channel blacker or a nitrate.

31. The composition according to claim 30, wherein the second therapeutic agent is amlodipine, atenolol, or nitroglycerine.

* * * * *

UNITED STATES PATENT AND TRADEMARK OFFICE
CERTIFICATE OF CORRECTION

| | | |
|---|---|---|
| PATENT NO. | : 7,943,620 B2 | Page 1 of 1 |
| APPLICATION NO. | : 12/075107 | |
| DATED | : May 17, 2011 | |
| INVENTOR(S) | : Scott L. Harbeson and Craig Masse | |

It is certified that error appears in the above-identified patent and that said Letters Patent is hereby corrected as shown below:

In Column 28, Claim 30, Line 11 delete "blacker" and insert --blocker--.

Signed and Sealed this
First Day of November, 2011

David J. Kappos
*Director of the United States Patent and Trademark Office*